United States Patent
Hell et al.

[11] Patent Number: 6,009,141
[45] Date of Patent: Dec. 28, 1999

[54] X-RAY COMPUTED TOMOGRAPHY APPARATUS WITH ELECTRONIC SCANNING OF A RING-SHAPED ANODE

[75] Inventors: Erich Hell, Erlangen; Peter Schardt, Roettenbach, both of Germany

[73] Assignee: Siemens Aktiengesellschaft, Munich, Germany

[21] Appl. No.: 09/080,350

[22] Filed: May 18, 1998

[30] Foreign Application Priority Data

May 26, 1997 [DE] Germany .......................... 197 21 981

[51] Int. Cl.[6] .................................................. G01N 23/00
[52] U.S. Cl. ............................................... 378/10; 378/137
[58] Field of Search ....................................... 378/10, 137

[56] References Cited

U.S. PATENT DOCUMENTS 5,247,556  9/1993  Eckert et al. .
5,504,791  4/1996  Hell et al. .
5,548,630  8/1996  Hell et al. .

FOREIGN PATENT DOCUMENTS 196 17 126  11/1997  Germany .

Primary Examiner—Craig E. Church
Attorney, Agent, or Firm—Hill & Simpson

[57] ABSTRACT

An x-ray computed tomography apparatus with electronic scanning of a ring-shaped anode has a solenoid coil for space-charge compensation which allows access to the anode. The solenoid coil is constructed of multiple parts so that a connector part can be released from a base part and the anode is thereby made accessible.

4 Claims, 3 Drawing Sheets

X-RAY COMPUTED TOMOGRAPHY APPARATUS WITH ELECTRONIC SCANNING OF A RING-SHAPED ANODE

BACKGROUND OF THE INVENTION

1. Field of the Invention

The present invention is directed to an x-ray computed tomography apparatus of the type having an elongated anode that is scanned by an electron beam for generating a traveling x-ray beam, this electron beam being generated by an electron gun, wherein the electron beam is deflected onto and guided along the anode by a magnet arrangement.

2. Description of the Prior Art

U.S. Pat. No. 5,548,630 discloses an x-ray computed tomography apparatus of the above general type.

An x-ray computed tomography apparatus with electronic scanning of an annular anode is also disclosed in U.S. Pat. No. 5,247,556.

Given a low space requirement, such computed tomography apparatuses enable an especially fast scanning of an examination subject because the focus is electronically guided around the anode. A static guidance field that holds the electrons on the predetermined circular orbit and a dynamic kick field that deflects the electrons onto the ring anode in the desired location are required for guidance and deflection of the electron beam.

Solenoid focusing can be provided so that the electron beam is kept constant in cross-section and so that a constant focal spot is achieved along the ring anode, this solenoid focusing being effected by a solenoid coil arranged along the ring-shaped path for the electron beam. This solenoid coil surrounds the ring anode.

SUMMARY OF THE INVENTION

An object of the present invention is to provide an x-ray computed tomography apparatus of the type initially described wherein easy access to the ring anode, for example for replacement thereof, is enabled given employment of a solenoid coil that surrounds the ring anode for keeping the cross-section of the electron beam constant.

The above object is achieved in accordance with the principles of the present invention in a computed tomography apparatus wherein the anode is surrounded by a solenoid coil, the solenoid coil being formed by a number of releasable coil parts which can be removed so as to allow access to the anode from an exterior of the solenoid coil.

In the inventive x-ray computed tomography apparatus, it is possible to open the solenoid coil so that access to the anode is gained. The solenoid coil itself is preferably manufactured of a metal having a low atomic number, for example aluminum, so that the x-rays can emerge from the anode through the solenoid coil toward the outside largely unattenuated.

DESCRIPTION OF THE PREFERRED EMBODIMENTS

Figure 1:
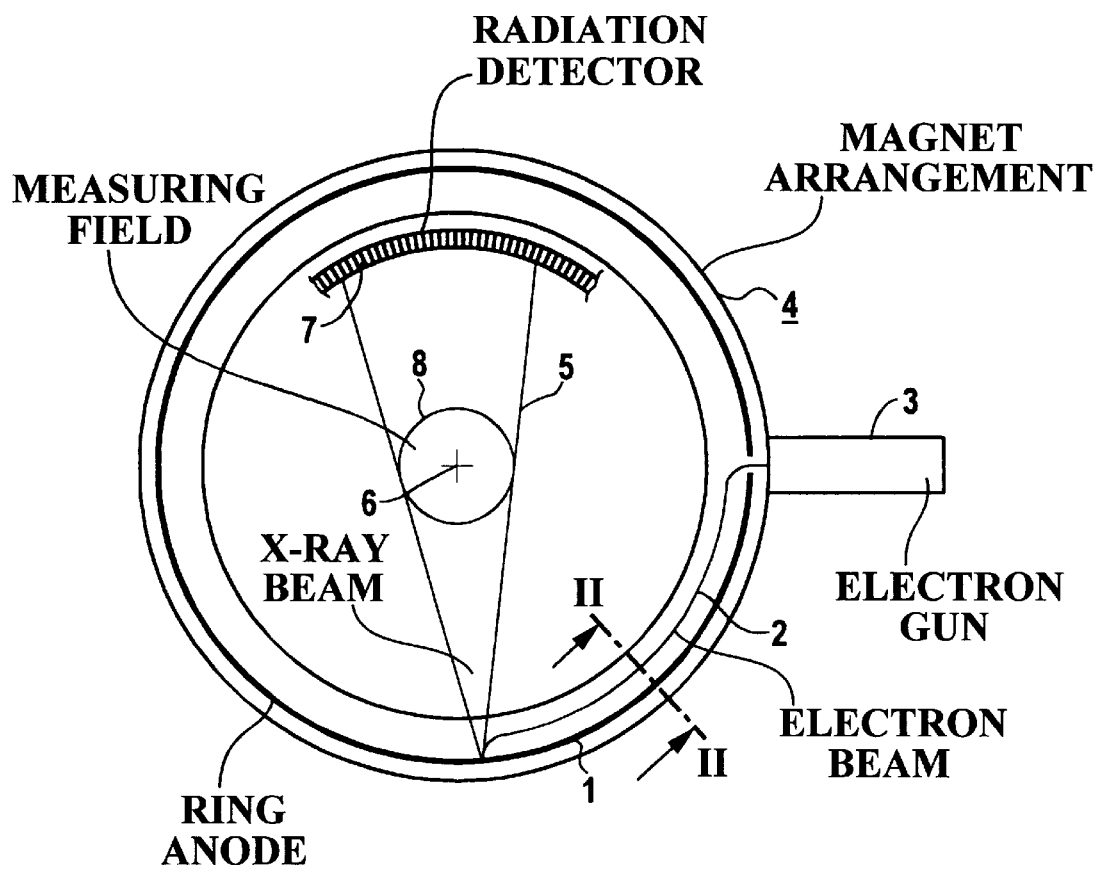
FIG. 1 shows basic components of an x-ray computed tomography apparatus for explaining the invention.

FIG. 1 shows the x-ray source of an x-ray computed tomography apparatus with a ring anode 1. The ring anode 1 is scanned by an electron beam 2 that is generated by an electron gun 3. An annularly fashioned magnet arrangement 4 guides the electron beam circularly and deflects ("kicks") it onto the ring anode 1. An x-ray beam 5 emanates from the focus (point of incidence of the electron beam 2 on the ring anode 1), this x-ray beam 5 being gated to form a fan-shaped beam in a known way, which rotates around the system axis 6. The x-ray beam 5 strikes an annular radiation detector 7 that generates electrical signals corresponding to the received radiation intensity and supplies these signals to a computer (not shown) that generates an image from these signals in a known manner of a patient arranged in the measuring field 8. So that the x-ray beam 5 can pass the radiation detector 7 when emerging from the x-ray source, the detector 7 is arranged laterally next to the exit window.

The magnet arrangement 4 is only schematically shown in FIG. 1. As can be seen from FIG. 2, which shows a section along II—II in FIG. 1, the magnet arrangement includes windings 9 for guidance of the electron beam 2 on a circular path that lie in recesses of cores 10 that are arranged at both sides of the electron beam 2. The cores 10 are surrounded by windings 11 that effect the deflection of the electron beam 2 onto the ring anode 1. Holders 12 hold the components 9, 10, 11 in a vacuum housing 13 that is closed vacuum-tight by a cover 14 by means of a seal 15.

For space-charge compensation, i.e. for keeping the cross-section of the electron 2 constant over its entire path, the electron beam 2 is surrounded by a solenoid coil 16.

Figure 2:
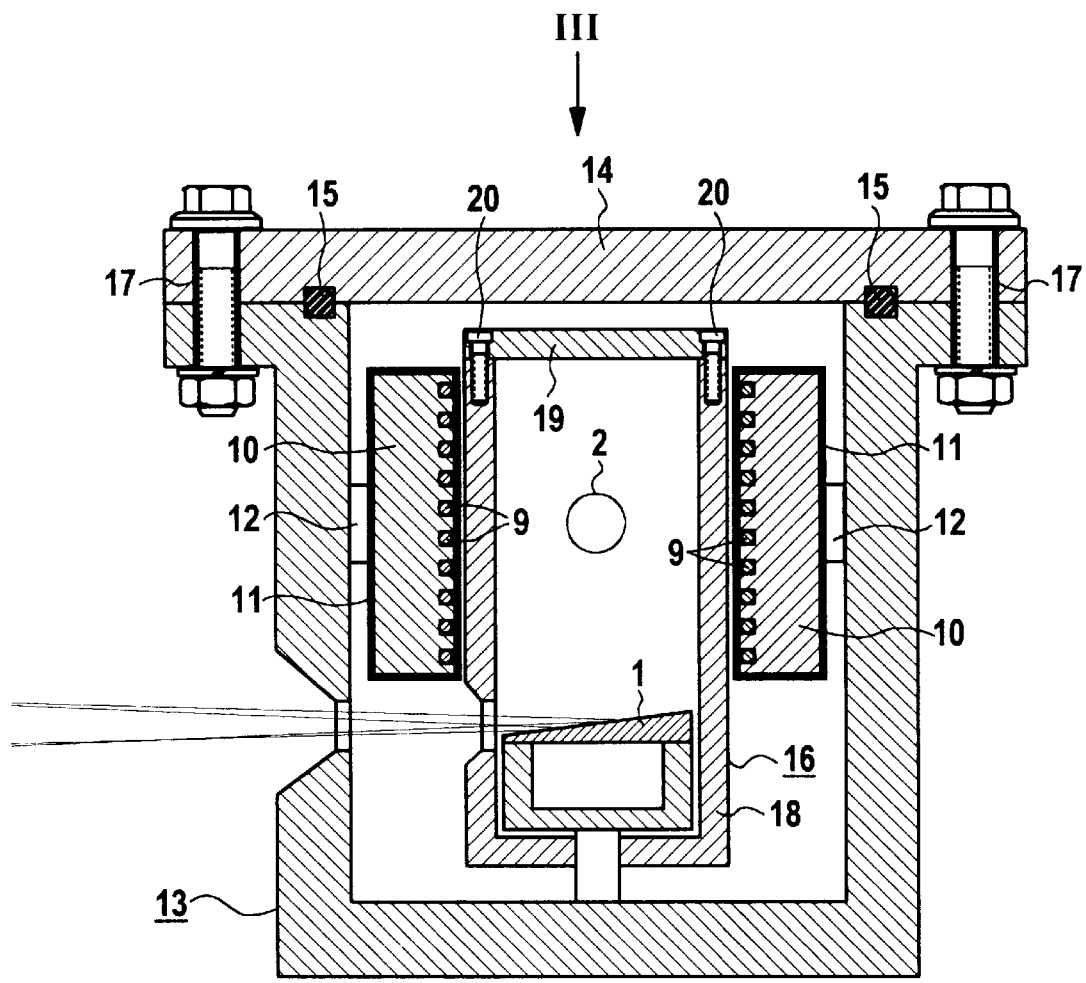
FIG. 2 is a cross-section through the vacuum part of the x-ray computed tomography apparatus of FIG. 1.
Figure 3:
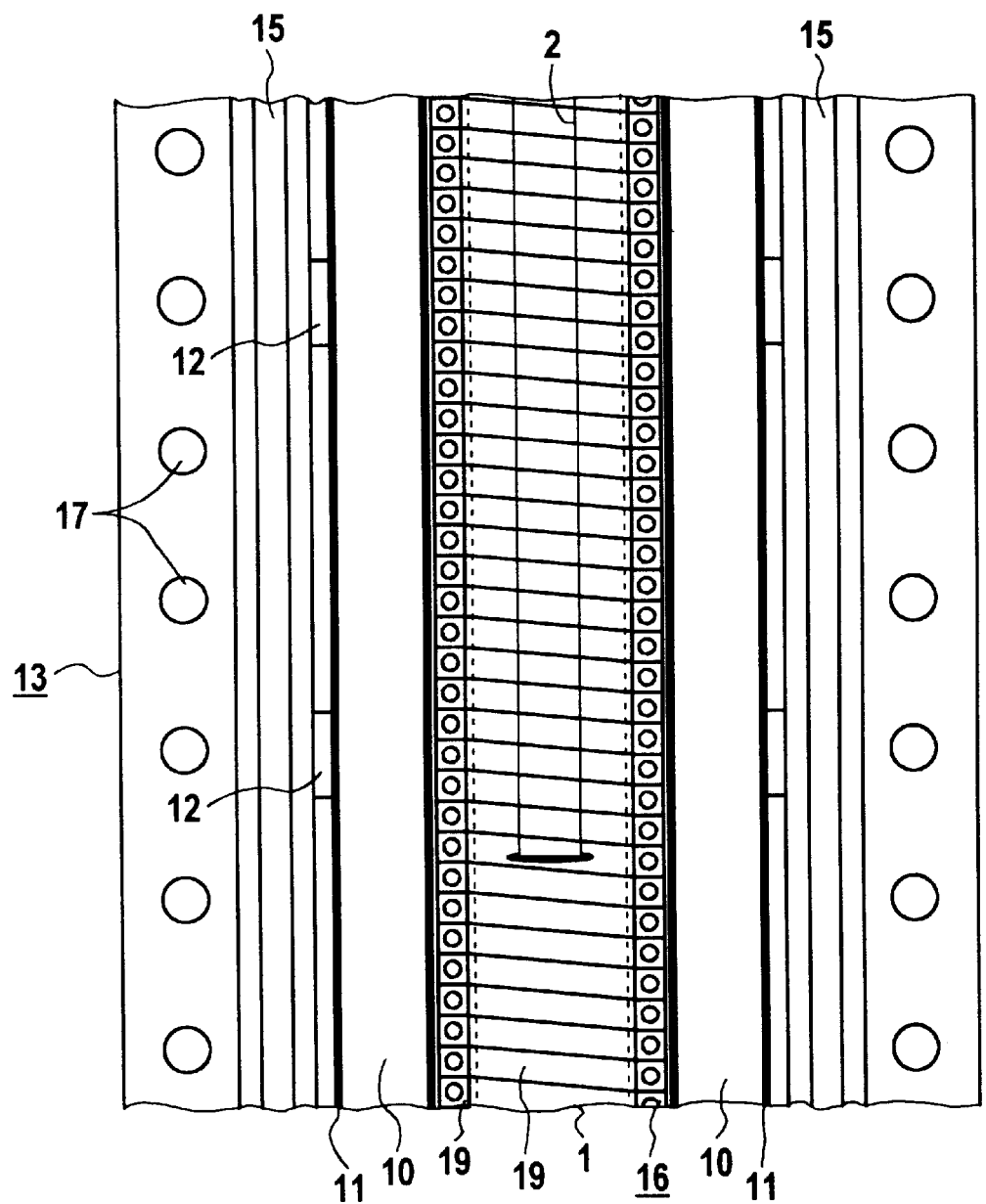
FIG. 3 is a plan view of the vacuum part according to FIG. 2 with the cover opened.

FIG. 3 shows a view in the direction of the arrow III in FIG. 2 with the cover 14 open, shown in a linear illustration. The circles 17 represent screw holes for the screws visible in FIG. 1.

It is important that the solenoid coil 16, which surrounds the entire path of the electron beam 2, have U-shaped bows 18 that are electrically conductively connected to one another by connector parts 19. The connector parts 19 are releasable by screws 20, so that access to the anode 1 is enabled.

The solenoid coil 16 is composed of a metal with a low atomic number, for example of aluminum, and has a smaller cross-section in the region of the exit of the x-rays so that the x-rays are not attenuated very much.

In the illustrated exemplary embodiment, the solenoid coil 16 is located inside the vacuum housing 13. It is also possible to arrange the coil 16 outside the vacuum housing, while still allowing the housing 13 to be opened. The solenoid coil 16 is shown as being curved, but can also be linear, for use in conjunction with a linear anode that is scanned by an electron beam, as shown in FIG. 3.

It proceeds from FIG. 3 that the connector parts 19 respectively connect preceding and following bows 18 to one another, so that a coil is thereby formed.

Although modifications and changes may be suggested by those skilled in the art, it is the intention of the inventors to embody within the patent warranted hereon all changes and modifications as reasonably and properly come within the scope of their contribution to the art.

We claim as our invention:

1. In an x-ray computed tomography apparatus having an elongated anode scanned by an electron beam emitted by an electron gun for producing a migrating x-ray beam, said electron beam being deflected onto and guided along said anode by an magnet arrangement, the improvement comprising:

a solenoid coil surrounding said anode, said solenoid coil being formed by a plurality of releasable coil parts which are removable for allowing access to said anode from an exterior of said solenoid coil.

2. The improvement of claim 1 wherein said solenoid coil comprises a plurality of U-shaped bows and a plurality of connector parts respectively releasably connected to said U-shaped bows, said connector parts respectively connecting adjacent ones of said U-shaped bows to each other.

3. The improvement of claim 1 wherein said solenoid coil is comprised of a metal having a low atomic number.

4. The improvement of claim 3 wherein said solenoid coil is comprised of aluminum.

* * * * *